United States Patent [19]

Blumental

[11] 4,136,284

[45] Jan. 23, 1979

[54] APPARATUS FOR EXAMINING A BODY BY MEANS OF PENETRATING RADIATION

[75] Inventor: Raphael Blumental, Kiriat Tivon, Israel

[73] Assignee: Elscint Ltd., Haifa, Israel

[21] Appl. No.: 807,175

[22] Filed: Jun. 16, 1977

[51] Int. Cl.² .............................................. G03B 41/16
[52] U.S. Cl. ................................. 250/445 T; 250/523
[58] Field of Search ............... 250/444, 445 R, 445 T, 250/446, 447, 522, 523, 524

[56] References Cited

U.S. PATENT DOCUMENTS 3,922,552  11/1975  Tedley ............................. 250/445 T Primary Examiner—Craig E. Church
Attorney, Agent, or Firm—Donald M. Sandler

[57] ABSTRACT

Apparatus for examining a body by means of penetrating radiation such as X- or γ- rays has a radiation beam assembly comprising a member with a radiation source for producing a collimated beam of penetrating radiation, and a member with detector means for receiving radiation from the source. Guide means slidably mount the members on a support structure containing a circle of reconstruction within which the body is located. The members are located on opposite sides of the center of the circle of reconstruction and are translatable as a unit in parallel paths to cause the beam to sweep through and define the plane of the circle of reconstruction. A flexible connection links the members together for maintaining a fixed spatial relationship therebetween during translation at least while the beam sweeps through the circle of reconstruction.

In one form of the invention, the flexible connection is constituted by a pair of belts to which the members are respectively attached, the belts being connected together at a common point. In another form of the invention, the flexible connection is constituted by a single belt.

11 Claims, 5 Drawing Figures

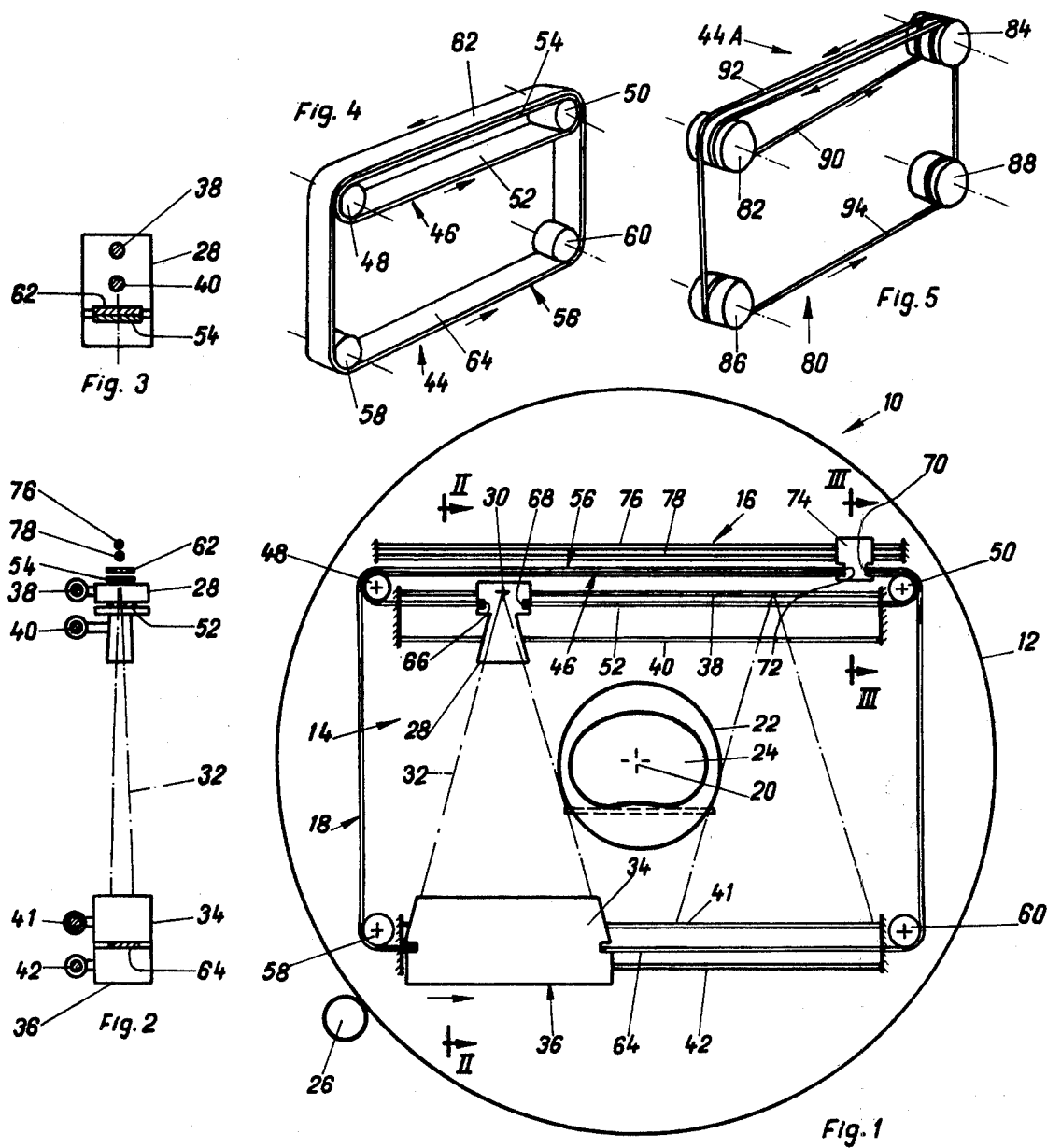

APPARATUS FOR EXAMINING A BODY BY MEANS OF PENETRATING RADIATION

BACKGROUND OF THE INVENTION

This invention relates to apparatus for examining a body by means of penetrating radiation, such as X- or γ-rays, to obtain the distribution of absorption coefficients with respect to the radiation in a plane passing through the body.

Such apparatus, hereinafter termed apparatus of the type described, is disclosed in U.S. Pat. Nos. 3,867,634 and 3,946,234. These patents disclose, respectively, a rectangular yoke and a C-shaped yoke which is slidably mounted on a support structure for bidirectional translation in a plane parallel to a circle of reconstruction within which a body to be examined is located. Rigidly attached to the yoke is a radiation beam assembly including a radiation source located on an arm of the yoke on one side of the center of the circle of reconstruction for producing a collimated beam of penetrating radiation, and detector means located on the opposite arm of the yoke for receiving radiation from the source passing through the circle of reconstruction. The structure is mounted for rotation about the center of the circle of reconstruction so that a body therein is scanned linearly by the collimated beam during translation of the yoke and at many different angles as the structure is rotated. The data produced by the detector means are processed in a computer in a known manner to provide the distribution of absorption coefficients over the plane of the circle of reconstruction.

The rectangular or C-shaped yoke provides a rigid mechanical coupling between the source and the detector means which maintains a fixed spatial relationship therebetween during translation of the radiation beam assembly on the support structure. Such relationship is critically important because relative displacement between the source and the detector means degrades the computed distribution of absorption coefficients. As a consequence of the geometrical considerations requiring a large radial dimension of the yoke, special designs must be resorted to in order to accomodate the resultant dynamic loadings due to the high accelerations experienced during the linear portion of the scanning operation as efforts are made to reduce scanning time.

Until the present, it has not been possible to reduce the physical size and mass of the coupling between the source and the detector means while maintaining the required rigidity therebetween during linear scans. It is therefore an object of the present invention to provide, in apparatus of the type described, new and improved coupling means which are more compact than the prior art, and which involves less mass and provides more favorable static moments than the coupling means of the prior art.

SUMMARY OF THE INVENTION

According to the present invention, a member with a radiation source for producing a collimated beam of penetrating radiation, and a member with detector means for receiving radiation from the source are slidably mounted on respective guides attached to the support so that the members are on opposite sides of the center of the circle of reconstruction and are translatable in parallel paths. A flexible connection links the members for maintaining a fixed spatial relationship therebetween during their translation on the support at least while the beam sweeps through the circle of reconstruction.

In one embodiment of the invention, the flexible connection includes a pair of belts to which the members are respectively attached, and the belts are connected together at a common point. In another embodiment of the invention, the flexible connection includes a single belt. Preferably, a counterweight is also attached to the flexible connection for translation in a direction opposite to the direction in which the members move.

The flexible connection of the present invention results in the reduction of static moments with respect to the two movable members, a reduction in rotational inertia of the members as well as a reduction in the over-all dimensions of the apparatus. The latter reduction is important when the source produces a fan beam with an apical angle of 30 degrees.

BRIEF DESCRIPTION OF DRAWINGS

Embodiments of the invention are disclosed in the accompanying drawings wherein:

FIG. 1 is an elevation view in schematic form of apparatus of the type described into which one embodiment of the invention is incorporated;

FIG. 2 is a section taken along the line II—II of FIG. 1;

FIG. 3 is a section taken along line III—III of FIG. 1;

FIG. 4 is a perspective schematic view of the first embodiment of the flexible connection which is shown in FIG. 1;

FIG. 5 is a perspective schematic view of a second embodiment of flexible connection according to the present invention.

DETAILED DESCRIPTION

Referring now to FIG. 1, reference numeral 10 designates apparatus of the type described comprising support structure 12, radiation beam assembly 14, guide means 16 and coupling means 18. Support structure 12 is a circular disc supported on peripheral bearings (not shown) for rotation about center 20 of the circle of reconstruction 22 within which body 24 is located. The periphery of structure 12 is toothed (not shown) for operative engagement with pinion 26 which selectively rotates the structure in a known manner.

Radiation beam assembly 14 includes member 28 with a radiation source 30 for producing a collimated beam of penetrating radiation such as x- or gamma- rays. The radiation is in the form of fan beam 32 which is essentially planar and defines the plane of the circle of reconstruction 22. In addition to member 28, assembly 14 includes member 34 with detector means 36 for receiving radiation from source 30.

Guide means 16 slideably mounts members 28 and 34 on support 12 for bi-directional translation in a plane parallel to the plane of the circle of reconstruction. Means 16 thus includes a pair of parallel rails 38, 40 lying in a plane parallel to the plane of reconstruction and rigidly attached to structure 12. These rails are located on one side of center 20 and are operatively associated with member 28 which is provided with bearings slideably receiving the rails. Means 16 also includes a pair of parallel rails 41, 42 rigidly attached to structure 12 and also lying in a plane parallel to the plane of the circle of reconstruction. These rails are located on the side of center 20 opposite to the side on which rails 38, 40 are located. Rails 41, 42 are operatively associated with member 34 which is provided with bearings slideably receiving the rails. As a consequence, members 28 and 34 are constrained for movement in planes parallel to the plane of reconstruction which is defined by the plane swept out by beam 32 as member 28 moves between terminal positions on rails 38, 40.

Coupling means 18 is a flexible connection (44 in FIG. 4) that links members 28 and 34 together for maintaining a fixed spatial relationship therebetween during translation of the radiation beam assembly on structure 12. In the embodiment of the invention shown in FIGS. 1 and 4, coupling means 18 is in the form of a pair of belts to which the members are respectively attached. Specifically, flexible connection 44 includes a first belt 46 operatively engaging a pair of spaced pulleys 48, 50 rotatably mounted on structure 12. The engagement is such that no slippage occurs. Belt 46 thus defines a pair of parallel runs 52, 54 each of which is located on one side of center 20. Connection 44 also includes a second belt 56 operatively engaged with pulleys 58, 60 rotatably mounted on structure 12, and operatively engaged with belt 46 where the latter is wrapped around pulleys 48, 50. The engagement of belt 56 with the portions of belt 46 wrapped around pulleys 48, 50 is such that no slippage occurs. Belt 56 defines a pair of runs 62, 64 parallel to runs 52, 54 of belt 46. The runs of belt 56, however, are located on opposite sides of center 20. Consequently, runs 62 and 54 of the belts overlie each other and no relative movement between the runs takes place.

Belt 46 is attached to member 28 by clamp means 66, 68 and to belt 56 by clamp means 70, 72 on counter-weight 74 which is slideably mounted on parallel rails 76, 78 rigidly connected to structure 12 and lying in a plane parallel to the plane of the circle of reconstruction. Rails 76, 78 are also parallel to rails 38, 40 and to runs 52 and 54 of belt 46, and to run 62 of belt 56. Finally, clamp means 70, 72 also attach belt 56 to the counter-weight which thus acts to connect the two belts together at a common point.

Belts 46 and 56 are preferably formed by stacking together a plurality of individual, very thin, flat steel bands. However, other types of flexible connections can be used. For example, chain or cable can be used since the moving masses are relatively small and elongation of the flexible connection is minimized by the utilization of counter-weight 74.

In operation, a reciprocating force is applied to member 34, preferably the heavier of the two members. Belts 46 and 56 transmit motion to members 28 and 34 so that both move in the same direction while counter-weight 74 moves in an opposite direction. As a result, a bi-directional translation of assembly 14 takes place causing beam 32 to sweep through the circle of reconstruction and thus linearly scan body 24. Linear scans are repeated at many different angular positions of the structure in a known manner. During all of these scans, the output of the detector means is supplied to a storage device (not sown) which stores the output of the detector means as a function of the linear displacement of the assembly with respect to the center of the circle of reconstruction, and as a function of the angular position of structure 12. In a known manner, the data acquired during scanning are processed to provide the distribution of absorption coefficients across the circle of reconstruction.

Counter-weight 74 moves in a direction opposite to the direction of movement of assembly 14 and serves to reduce the tensile stress in belt 56 when the angular position of structure 12 is such that the direction of linear scan is inclined to the horizontal. In this way, when counter-weight 74 has a mass equal to the mass of member 28, only belt 46 is subject to gravitational forces, while belt 56 transmits acceleration forces only. Thus, an any angular position of the structure 12, belt 56 is under minimal tensile stress during a constant velocity traverse of the circle of reconstruction. Thus, elastic deformation in the belts is minimized. Alternatively, one of the pulleys, e.g., pulley 48, is selectively powered in one direction or the other by a motor (not shown).

Alternative to the flexible connection 44, connection 44A in the second embodiment shown in FIG. 5 can be used. In such case, a single belt 80 is employed together with four pulleys 82, 84, 86, 88 rotatably mounted on the support structure. Belt 80 is wrapped twice around two of the pulleys, i.e., pulleys 82, 84, located on one side of the center of the circle of reconstruction. The belt also passes around pulleys 86, 88 located on the other side of the center. Belt 86 thus defines a number of parallel runs associated with pulleys 82, 84 (specifically, runs 90 and 92) and run 94 associated with pulleys 82, 86. Runs 90, 92, and 94 of belt 80 correspond respectively to runs 46, 54/62 and 61 of belts 46, 56 of connection 44. Members 28 and 34 are connected to the runs of belt 80 in the same manner as the members are connected to corresponding runs of belts 46 and 56.

It is believed that the advantages and improved results furnished by the apparatus of the present invention are apparent from the foregoing description of the several embodiments of the invention. Various changes and modifications may be made without departing from the spirit and scope of scope of the invention as sought to be defined in the claims that follow.

What is claimed is:

1. In apparatus for examining a body by means of penetrating radiation such as X- or γ- rays, a radiation beam assembly comprising a member with a radiaton source for producing a collimated beam of penetrating radiation, a member with detector means for receiving radiation from the source, and guide means for slidably mounting the members on a support structure containing a circle of reconstruction within which the body is located so that the members are on opposite sides of the center of the circle of reconstruction and so that the members are translatable as a unit in parallel paths to cause the beam to sweep through and define the plane of the circle of reconstruction, the improvement comprising a flexible connection linking the members for maintaining a fixed spatial relationship therebetween during their translation at least while the beam sweeps through the circle of reconstruction.

2. The invention of claim 1 wherein the flexible connection includes a pair of belts to which the members are respectively attached, and means for connecting the belts together at a common point.

3. The invention according to claim 1 wherein the flexible connection includes a first belt operatively engaged with a first pair of pulleys for defining a pair of parallel runs each of which is located on one side of the center of the circle of reconstruction, and a second belt operatively engaged with the first pair of pulleys and operatively engaged with a second pair of pulleys for defining a pair of runs parallel to the runs of the first belt, the runs of the second belt being located on opposite sides of the center of the circle of reconstruction, means for connecting the belts together for constraining the parallel runs of the belts against relative movement in the direction of the runs, and means connecting one of the members to a run of the first belt, and means for connecting the other of the members to a run of the second belt on the opposite side of the center of the circle of reconstruction.

4. The invention of claim 3 wherein the coupling means includes a counterweight connected to the belt such that movement of the members in one direction causes movement of the counterweight in the opposite direction.

5. The invention of claim 4 wherein the belts are connected together at the counterweight.

6. The invention of claim 5 wherein the guide means mount the members for slidable movement in the direction of the parallel runs.

7. The invention of claim 6 wherein the support structure is rotatable about the center of the circle of reconstruction.

8. The invention of claim 1 wherein the flexible connection includes a single belt, and a plurality of pulleys in operative relationship therewith defining spaced parallel runs that lie on opposite sides of the circle of reconstruction, the members being connected respectively to the parallel runs of the belt.

9. Apparatus for examining a body by means of penetrating radiation such as X- or γ- rays, comprising
(a) a structure defining a circle of reconstruction within which a body to be examined can be placed and rotatable about the center of the circle of reconstruction;
(b) a radiation beam assembly mounted on the structure including a member with a radiation source on one side of the center of the circle of reconstruction for producing a beam of penetrating radiation; and a member with detector means on the other side of the center of the circle of reconstruction for receiving radiation from the source passing through the circle of reconstruction;
(c) guide means for slidably mounting the members on the support structure so that the members are on opposite sides of the center of the circle of reconstruction and so that the members are translatable in parallel paths; and
(d) flexible connection means linking the source to the detector means for maintaining a fixed spatial relationship therebetween and for effecting bidirectional translation of the assembly on the structure at least while radiation from the source passes through the circle of reconstruction.

10. Apparatus according to claim 9 wherein the flexible connection includes a pair of belts to which the members are respectively attached, and means for connecting the belts together at a common point.

11. Apparatus according to claim 9 wherein the flexible connection includes a single belt, and a plurality of pulleys in operative relationship therewith defining parallel runs that lie on opposite sides of the circle of reconstruction, the members being connected respectively to the parallel runs of the belt.

* * * * *